(12) United States Patent
Kobayashi et al.

(10) Patent No.: US 7,910,762 B2
(45) Date of Patent: Mar. 22, 2011

(54) ASYMMETRIC REACTION CATALYST AND METHOD FOR PREPARING OPTICALLY ACTIVE COMPOUND USING THE SAME

(75) Inventors: Shu Kobayashi, Tokyo (JP); Haruro Ishitani, Tokyo (JP); Yasuhiro Yamashita, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 12/567,936

(22) Filed: Sep. 28, 2009

(65) Prior Publication Data

US 2010/0029968 A1 Feb. 4, 2010

Related U.S. Application Data

(62) Division of application No. 10/589,259, filed as application No. PCT/JP2005/004077 on Mar. 9, 2005, now Pat. No. 7,667,078.

(30) Foreign Application Priority Data

Mar. 9, 2004 (JP) .................................. 2004-064994

(51) Int. Cl.
*C07F 9/00* (2006.01)
(52) U.S. Cl. ........... 556/42; 564/413; 564/431; 568/719
(58) Field of Classification Search .......................... None
See application file for complete search history.

(56) References Cited

U.S. PATENT DOCUMENTS

| | | |
|---|---|---|
| 6,812,352 B2 | 11/2004 | Kreutzer et al. |
| 7,084,293 B2 | 8/2006 | Rosier et al. |
| 7,351,831 B2 | 4/2008 | Kobayashi et al. |
| 7,667,078 B2 | 2/2010 | Kobayashi et al. |
| 2007/0265472 A1 | 11/2007 | Kobayashi et al. |

FOREIGN PATENT DOCUMENTS

| | | |
|---|---|---|
| JP | 4-91093 | 3/1992 |
| JP | 11-33407 | 2/1999 |
| JP | 2001-031682 | 2/2001 |
| JP | 2001-252568 | 9/2001 |
| JP | 2002-275112 | 9/2002 |
| JP | 2002-356454 | 12/2002 |
| JP | 2003-299962 | 10/2003 |
| WO | WO2005/084803 | 9/2005 |

OTHER PUBLICATIONS

Matsunaga et al., {Catalytic Enantioselective meso-Epoxide Ring Opening Reaction with Phenolic Oxygen Nucleophile Promoted by Gallium Heterobimetallic Multifunctional Complexes, Journal of the American Chemical Society (2000), 122(10), 2252-2260}.*
Soneet al., { Inclusion properties of acyclic phenol-formaldehyde oligomer analogs containing 2,2'-dihydroxybiphenyl or 2,2'-dihydroxy-1,1'-binaphthyl unit, Bulletin of the Chemical Society of Japan (1994), 67(12), 3366-3369}.*

Andrade et al., "Niobium (V) chloride-mediated allylation of aldehydes. Scope and stereoselectivity," Tetrahedron Letters. vol. 42, No. 37 pp. 6473-6476 (2001).
Arai et al., "A Simple and Regioselective Carbon-Oxygen Bond Cleavage Using Niobium(V)," Synlett. vol. 6 pp. 1104-1106 (2004).
Database WPI Week 200281, Derwent Publications Ltd., XP002424390, AN 2002 746136, London, Great Britain.
Howarth et al., "Lewis Acid Catalysis of the Diels-Alder Reaction Using Niobium and Tantalum Chlorides in the Presence of Coordinating Ligands," Molecules. vol. 5 pp. 993-997 (2000).
International Preliminary Report on Patentability corresponding to International Application No. PCT/JP2005/004077 dated Sep. 13, 2006.
International Search Report corresponding to International Patent Application No. PCT/JP2005/004077 dated Jul. 12, 2005.
Ishitani et al., "Efficient Catalytic Enantioselective Mannich-Type Reactions Using a Zirconium-Bis(binaphthol)methane Complex," Tetrahedron Letters. vol. 40 pp. 2161-2164 (1999).
Kobayashi et al., "A Novel Dinuclear Chiral Niobium Complex for Lewis Acid Catalyzed Enantioselective Reactions: Design of a Tridentate Ligand and Elucidation of the Catalyst Structure," Angewandte Chemie International Edition. vol. 44, No. 5 pp. 761-764 (2005).
Kobayashi et al., "Silyl Enol Ethers," Science of Synthesis: Houben-weyl Methods of Molecular Transformations. vol. 4 p. 317 (2002).
Maruoka et al., "Chiral Helical Lewis Acids for Asymmetric Diels-Alder Catalysts," J. Org. Chem. vol. 58, No. 11 pp. 2938-2939 (1993).
Notice of Allowance corresponding to U.S. Appl. No. 10/589,259 dated Oct. 21, 2009.
Official Action corresponding to U.S. Appl. No. 10/589,259 dated May 5, 2008.
Official Action corresponding to U.S. Appl. No. 10/589,259 dated Jul. 9, 2008.
Official Action corresponding to U.S. Appl. No. 10/589,259 dated Mar. 31, 2009.
Supplementary European Search Report corresponding to European Patent Application No. 05720349.9-2104 dated Mar. 27, 2007.
Written Opinion of the International Searching Authority corresponding to International Patent Application No. PCT/JP2005/004077 dated Jul. 12, 2005.
Yamashita et al., "Highly anti-selective asymmetric aldol reactions using chiral zirconium catalysts. Improvement of activities, structure of the novel zirconium complexes, and effect of a small amount of water for the preparation of the catalysts," Journal of the American Chemical Society. vol. 124, No. 13 pp. 3292-3302 (2002).

* cited by examiner

*Primary Examiner* — Daniel M Sullivan
*Assistant Examiner* — Chukwuma O Nwaonicha
(74) *Attorney, Agent, or Firm* — Jenkins, Wilson, Taylor & Hunt, P.A.

(57) ABSTRACT

An asymmetric reaction catalyst is obtained by mixing a pentavalent niobium compound and an optically active triol or tetraol having a binaphthol structure of R or s configuration, and the triol is represented by the following formula: (I)

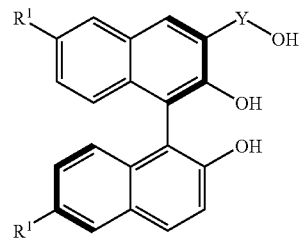

wherein, Y is divalent hydrocarbon and $R^1$ is a hydrogen atom, a halogen atom, a trifluoromethyl group, or an alkyl group or alkoxy group having at most 4 carbons.

10 Claims, 2 Drawing Sheets

Scheme 1 Synthesis of 8a

ASYMMETRIC REACTION CATALYST AND METHOD FOR PREPARING OPTICALLY ACTIVE COMPOUND USING THE SAME

CROSS REFERENCE TO RELATED APPLICATIONS

This application is a divisional patent application of U.S. patent application Ser. No. 10/589,259, filed May 23, 2007, now U.S. Pat. No. 7,667,078 which is a national stage application of International Application No. PCT/JP2005/004077, filed Mar. 9, 2005, and which claims benefit of Japanese Patent Application No. 2004-064994 filed Mar. 9, 2004, the disclosures of each of which are incorporated herein in their entirety.

BACKGROUND OF THE INVENTION

1. Field of the Invention

The present invention relates to an asymmetric reaction catalyst and a method for preparing an optically active compound. In particular, the present invention relates to an asymmetric reaction catalyst used in nucleophilic addition and a method for preparing an optically active compound.

2. Description of the Related Art

Asymmetric nucleophilic addition reactions to the unsaturated carbon of a C═O bond or C═N bond (for example, imine (C═N) or hydrazone (C═N—N) compound) in the presence of a Lewis acid catalyst results in the formation of a new carbon-carbon bond. These reactions have been heavily examined because they can be used in the synthesis of various optically active compounds. Also, from the viewpoints of selectivity and stability, various metals and ligands are used as the above-mentioned catalyst. The inventors of the present invention have already developed an asymmetric catalyst prepared from a zirconium alkoxide and a binaphthol derivative and have reported that asymmetric Diels-Alder reactions (for example, refer to Japanese Patent Laid-open Publication 2002-356454), aldol reactions (for example, refer to Japanese Patent Laid-open Publication 2000-67833 and Yamashita et al., *J. Am. Chem. Soc.*, 2002, Vol. 124, page 3292) and imino aldol reactions (for example, refer to Japanese Patent Laid-open Publication HII-33407) can be carried out with high yields and high stereoselectivity.

Also, it is expected that niobium has a high Lewis acidity (for example refer to C. Andrade, *Tetrahedron Lett.*, 2001, Vol. 42, page 6473) and an example of an asymmetric Diels-Alder reaction carried out using niobium in the catalyst has been reported (for example, refer to J. Howarth and K. Gillespie, *Molecules*, 2000, Vol. 5, page 993).

SUMMARY OF THE INVENTION

However, effective catalysts are desired for the purpose of developing more effective reactions, in other words, reactions having chemical yields close to 100% and stereoselectivity close to 100%.

An object of the present invention is to solve the above-mentioned problem by providing an asymmetric reaction catalyst which achieves superior yields and superior stereoselectivity as well as being easy to handle and by also providing a method for preparing an optically active compound using the same. The inventors have found that an asymmetric catalyst having niobium as the active central metal can be obtained by mixing a niobium compound and a triol or tetraol having an optically active binaphthol structure. Also, the inventors have found that this catalyst is suitable for asymmetric nucleophilic addition reactions.

The asymmetric reaction catalyst of the present invention is obtained by mixing a pentavalent niobium compound and a triol or tetraol having an optically active binaphthol structure of R or S configuration. Preferably, the above-mentioned niobium compound is represented by the formula $NbX_5$ (wherein, X represents an alkoxide or a halogen atom).

Preferably, the above-mentioned triol is represented by the following formula (I):

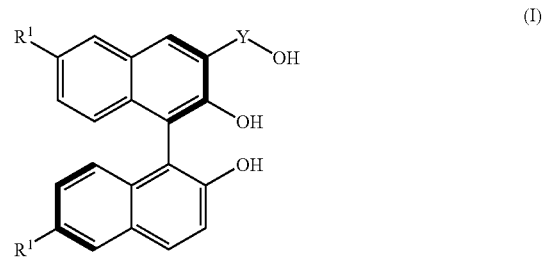

(I)

wherein, Y represents a divalent hydrocarbon group and $R^1$ represents a hydrogen atom, a halogen atom, a perfluoroalkyl group having at most four carbons, or an alkyl group or alkoxy group having at most 4 carbons, or is represented by the following formula (II):

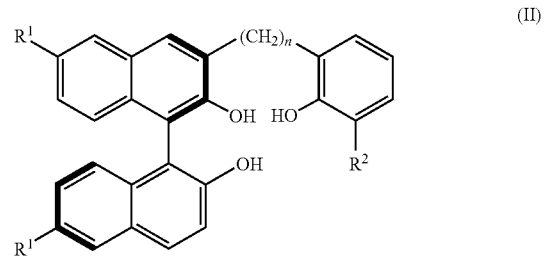

(II)

wherein, $R^1$ represents a hydrogen atom, a halogen atom, a perfluoroalkyl group having at most 4 carbons, or an alkyl group or an alkoxy group having at most four carbons; $R^2$ represents a hydrogen atom or a hydrocarbon group having 1 to 10 carbons; and n is an integer from 0 to 2.

Preferably, the above-mentioned tetraol is represented by the following formula (III):

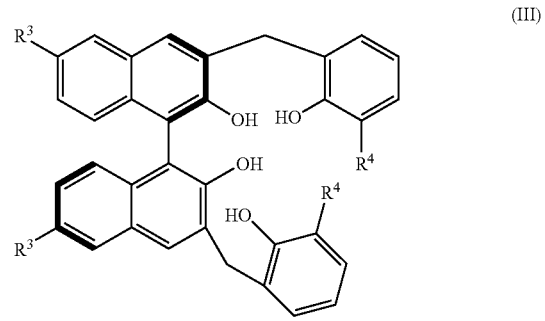

(III)

wherein, $R^3$ represents a hydrogen atom, a halogen atom, a perfluoroalkyl group having at most 4 carbons, or an alkyl group or alkoxy group having at most 4 carbons and $R^4$ represents a hydrogen atom or a hydrocarbon group having 1 to 10 carbons.

In the method for preparing a optically active compound of the present invention, a reaction substrate represented by $R^5R^6C=N-Z$ (wherein $R^5$ and $R^6$, not being the same, are selected from the group consisting of a hydrogen atom, a hydrocarbon group, an alkoxycarbonyl group, and a hydrocarbon group having a functional group and Z represents an aryl group or an acylamino group) and a nucleophilic agent are reacted by nucleophilic addition using the above-mentioned asymmetric reaction catalyst.

Preferably, the above-mentioned reaction substrate is an imine represented by the following formula (IV):

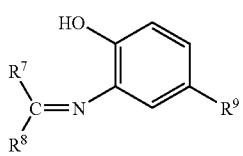

(IV)

wherein, $R^7$ and $R^8$, not being the same, are selected from the group consisting of a hydrogen atom, a hydrocarbon group, and a hydrocarbon group having a functional group and $R^9$ represents a hydrogen atom or a trifluoromethyl group, or the above-mentioned reaction substrate is a benzoylhydrazone represented by the following formula (V):

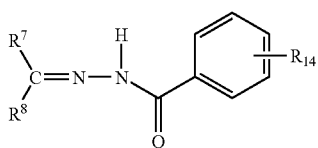

(V)

wherein, $R^7$ and $R^8$, not being the same, are selected from the group consisting of a hydrogen atom, a hydrocarbon group, and a hydrocarbon group having a functional group and $R^{14}$ represents a hydrogen atom or a substituent having an 25 electron-withdrawing property.

Preferably, the above-mentioned nucleophilic agent is a silicon enolate represented by the following formula (VI):

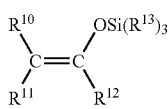

(VI)

wherein $R^{10}$ and $R^{11}$ are each independently one selected from the group consisting of a hydrogen atom, an aliphatic hydrocarbon group, an aromatic hydrocarbon group, an alkyloxy group, an aryloxy group, and an silyloxy group; $R^{12}$ is one selected from the group consisting of a hydrogen atom, an aliphatic hydrocarbon group, an alkyloxy group, an aryloxy group, an arylthio group, and a alkylthio group; and each $R^{13}$, being the same or different, represents a hydrocarbon group.

Preferably, the above-mentioned method for preparing the optically active compound is carried out by adding an imidazole derivative and/or a synthetic crystalline zeolite to the reaction system.

In the method for preparing an optically active compound of the present invention, a reaction substrate and a nucleophilic agent are reacted by nucleophilic addition using the above-mentioned asymmetric reaction catalyst.

Preferably, the above-mentioned reaction substrate is an epoxide, the above-mentioned nucleophilic agent is a nitrogen compound, and the optically active compound is a nitrogen-containing compound.

In accordance with the present invention, an asymmetric reaction catalyst which achieves superior yields and superior stereoselectivity as well as being easy to handle can be obtained. Also, an optically active compound can be efficiently prepared by an asymmetric nucleophilic addition reaction using this catalyst. Furthermore, a selective reaction can be carried out without the occurrence of side reactions because the reaction is mild.

DETAILED DESCRIPTION OF THE INVENTION

Figure 1:
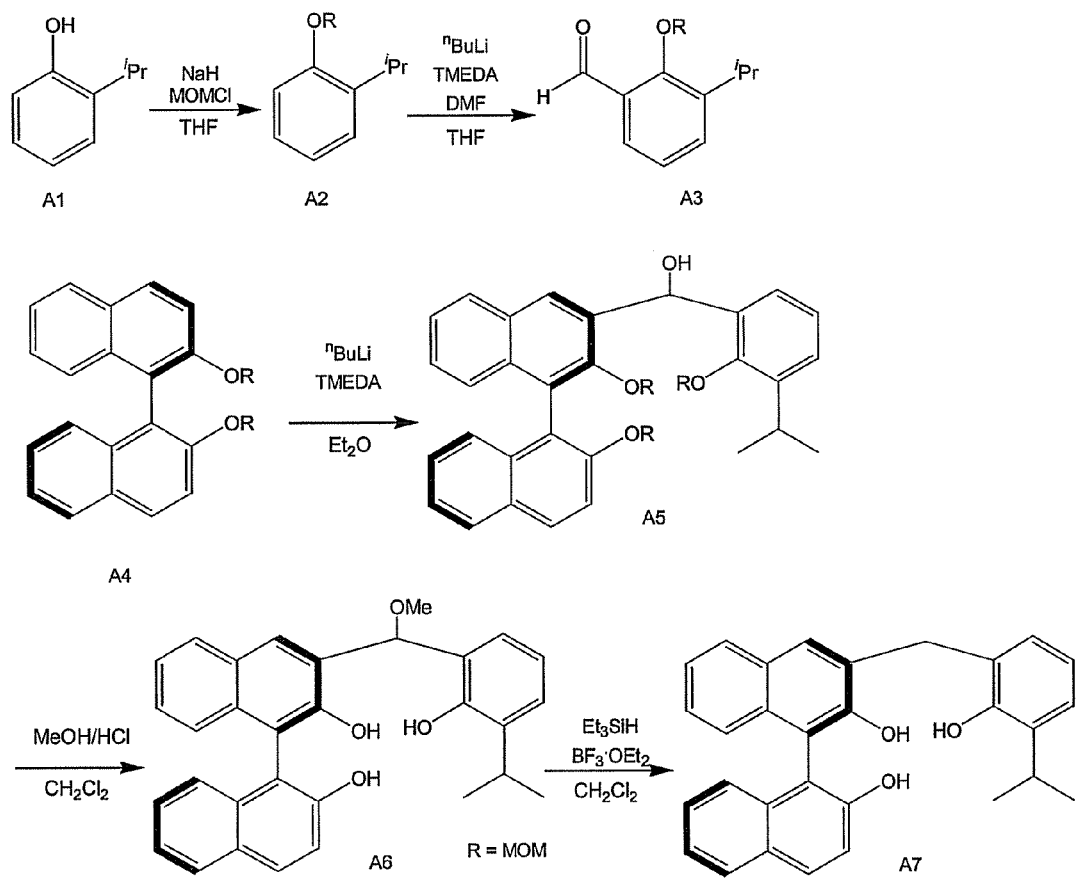
FIG. 1 shows a reaction scheme in order to prepare a triol having a binaphthol structure.

The embodiments of the present invention will now be explained.

Niobium Compound

There are no particular limitations as to what can be used as the pentavalent niobium compound in the present invention. Examples include compounds represented by the formula $NbX_5$ (wherein, X is an alkoxide or a halogen atom). Among these, from the viewpoint of ease of handling, Nb alkoxides (in particular, Nb methoxide or Nb ethoxide) are preferable.

Triol Having a Binaphthol Structure

The triol having a binaphthol structure used in the present invention includes an optically active binaphthol skeleton of R configuration or S configuration. By mixing this triol with the above-mentioned niobium compound, an asymmetric niobium catalyst is formed having a structure in which the optically active triol is bonded to an atom of niobium, which is the central metal, via an oxygen atom. Here, by finely adjusting the distance between the binaphthol ring and the phenol as well as by finely adjusting the substituent of the phenol, catalyst structures suitable for various nucleophilic addition reactions can be formed.

For example, a compound represented by the following formula (I):

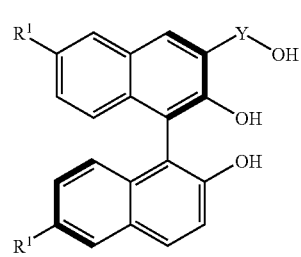

(I)

wherein, Y represents a divalent hydrocarbon group and $R^1$ represents a hydrogen atom, a halogen atom, a perfluoroalkyl group having at most 4 carbons, or an alkyl group or alkoxy group having at most 4 carbons, or a compound represented by the following formula (II):

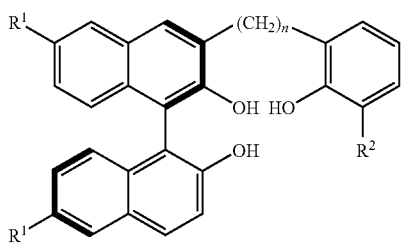

(II)

wherein, $R^1$ represents a hydrogen atom, a halogen atom, a perfluoroalkyl group having at most 4 carbons, or an alkyl group or alkoxy group having at most 4 carbons; $R^2$ represents a hydrogen atom or a hydrocarbon group having 1 to 10 carbons; and n is an integer from 0 to 2; can be suitably used as the above-mentioned triol. Specific examples include triols wherein, $R^2$ is one selected from the group consisting of hydrogen, a methyl group, t-butyl, and an isopropyl group and n=0 or 1.

Tetraol Having a Binaphthol Structure

The tetraol having a binaphthol structure used in the present invention includes an optically active binaphthol skeleton of R configuration or S configuration. By mixing this tetraol having a binaphthol structure with the above-mentioned niobium compound, an asymmetric catalyst is formed having a structure in which the optically active tetraol is bonded to an atom of niobium, which is the central metal, via an oxygen atom. By finely adjusting the distance between the binaphthol ring and the phenol as well as by finely adjusting the substituent of the phenol, catalyst structures suitable for various nucleophilic addition reactions can be formed.

For example, a compound represented by the following formula (III):

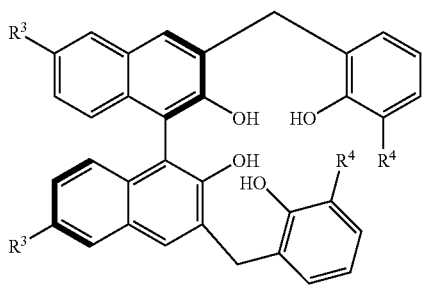

(III)

wherein, $R^3$ represents a hydrogen atom, a halogen atom, a perfluoroalkyl group having at most 4 carbons, or an alkyl group or alkoxy group having at most 4 carbons and $R^4$ represents a hydrogen atom or a hydrocarbon group having 1 to 10 carbons, can be suitably used as the above-mentioned tetraol. Examples of $R^3$ include hydrogen, a methyl group, and iodine. Examples of $R^4$ include hydrogen, a methyl group, t-butyl, and an isopropyl group.

Examples of the substituent (above-mentioned $R^1$ and $R^3$) on the naphthalene ring in the above-mentioned triol or tetraol include a hydrogen atom, a halogen, an alkyl group, and a perfluoroalkyl group. Specific examples of a binaphthol structure having this type of substituent include 3,3'-dibromo-, 6,6'-dibromo-, 3,3'-dibromo-6,6'-diiodo-, 3,3'-methyl-, 6,6'-dimethyl-, and 3,3',6,6'-tetraiodo-1, 1'-bi-2-naphthol.

The role of the substituent on the naphthalene ring is considered to mainly be an electronic effect. There is no influence merely by the ease of positioning.

Preparation of the Catalyst

The mixed ratio of the above-mentioned niobium compound and the above-mentioned triol or tetraol is preferably 1/1 to 1/2 (niobium compound/triol or tetraol) and more preferably 1/1 to 1/1.3.

There are no particular limitations to the method for mixing the above-mentioned niobium compound and the above-mentioned triol or tetraol. Normally, the above-mentioned compounds can be mixed in an organic solvent and arbitrarily stirred. Hydrocarbons and halogenated hydrocarbons can be suitably used as the organic solvent. In particular, methylene chloride, toluene, or their mixture is suitable. There are no particular limitations to the mixing temperature. It is easy to mix close to room temperature and then it is suitable to heat to a temperature between room temperature and the boiling point of toluene (preferably around 60° C.) for aging. The heating time of the catalyst is normally in the range from 30 minutes to 24 hours and preferably in the range from 1 to 3 hours.

Other Components

If a nitrogen-containing compound is further added to asymmetric catalysts consisting of the above-mentioned niobium compound and the triol or tetraol, the catalytic properties become better. Preferably, the nitrogen containing compound is a pyridines (for example, pyridine, 2,6-Lutidine, 2,4,6-Collindine, or the like), a quinolines (for example, quinoline or isoquinoline, $^i$Pr2NEt, or an imidazoles (for example, N-methylimidazole). It preferable that the amount of these nitrogen-containing compounds added is approximately the same number of moles as the above-mentioned niobium compound. There are no particular limitations to the timing when these nitrogen containing compounds are added to the reaction system. Normally, it is preferable that these nitrogen-containing compounds are either mixed with the triol or tetraol before addition of the niobium compound or are added between the mixing of the triol or tetraol with the niobium compound and the addition of the nucleophilic agent.

Also, the catalytic properties of asymmetric catalysts consisting of the above-mentioned niobium compound and the above-mentioned triol or tetraol can be improved by further adding a synthetic crystalline zeolite such as molecular sieves. Normally, 3 A or 4 A are suitable as the molecular sieves.

Reaction Substrate

The catalyst of the present invention which has been prepared as above has a catalytic action for various asymmetric reactions. Examples include asymmetric Mannich reactions, epoxide asymmetric ring opening reactions, asymmetric allylation reactions, asymmetric Michael reactions, asymmetric cyanation reactions, and asymmetric alkylation reactions. In particular, the target product can be obtained in high yield and high stereoselectivity when the catalyst of the present invention is used in asymmetric Mannich reactions and epoxide asymmetric ring opening reactions.

Mannich Reaction

The catalyst of the present invention is particularly effective in a Mannich reaction where the electrophilic agent (reaction substrate) is an imine or an acylhydrazone and the nucleophilic agent is silicon enolate. An optically active nitrogen-containing compound is formed by this asymmetric reaction.

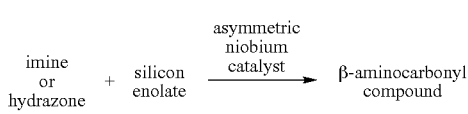

Reaction Substrate

Examples of the reaction substrate include compounds represented by $R^5R^6C=N-Z$ (wherein, $R^5$, $R^6$, and Z have the same definition as above and $R^5 \neq R^6$). These compounds are collectively termed imines and acylhydrazones.

When these compounds are used, the substituents $R^5$ and $R^6$ in the above-mentioned formula are each independently one selected from the group consisting of a saturated or an unsaturated aliphatic hydrocarbon group, an aromatic hydrocarbon group, and an alkoxycarbonyl group. These substituents may have a heteroatom or a functional group which does not inhibit the addition reaction. Each type of imine compound can be easily synthesized by the corresponding carbonyl compound and amine following an already known method. Similarly, each type of acylhydrazone compound can be easily synthesized from the corresponding carbonyl compound and acylhydrazine following an already known method.

Nucleophilic Agent

A silicon enolate can be suitably used as the nucleophilic agent. When the above-mentioned compound ($R^5R^6C=N-Z$) is the reaction substrate and a silicon enolate is used as the nucleophilic agent, an optically active β-aminocarbonyl compound or an optically active β-amino acid derivative can be obtained.

Imine

The imine used has been obtained by a dehydration reaction between an aldehyde or ketone and a primary amine. For example, an imine represented by the following formula (IV):

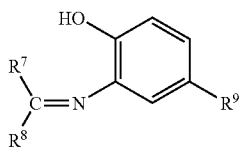

(IV)

(wherein, $R^7$ and $R^8$, not being the same, are selected from the group consisting of a hydrogen atom, a hydrocarbon group, and a hydrocarbon group having a functional group and $R^9$ represents a hydrogen atom or a trifluoromethyl group) can be suitably used. An imine where either $R^7$ or $R^8$ is a hydrogen atom is particularly suitable.

Silicon Enolate

Examples include a silicon enolate represented by the following formula (VI):

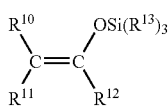

(VI)

(wherein $R^{10}$ and $R^{11}$ are each independently one selected from the group consisting of a hydrogen atom, an aliphatic hydrocarbon group, an aromatic hydrocarbon group, an alkyloxy group, an aryloxy group, and an silyloxy group; $R^{12}$ is one selected from the group consisting of a hydrogen atom, an aliphatic hydrocarbon group, an alkyloxy group, an aryloxy group, an arylthio group, and a alkylthio group; and each $R^{13}$, being the same or different, represents a hydrocarbon group).

In particular, a silicon enolate is preferable wherein, at least one of the $R^{13}$, which may be same or different, is selected from the group consisting of a methyl group, an ethyl group, an isopropyl group, a phenyl group, and a tertiary butyl group.

A β-aminocarbonyl compound having, for example, the following structure:

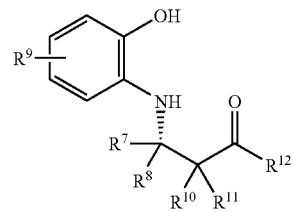

can be obtained by using the asymmetric niobium catalyst of the present invention when the above-mentioned imine and the above-mentioned enolate are used. When $R^{12}$ represents a hydrocarbon group, this product is a β-amino ester and when $R^{12}$ represents a thioalkoxy group, this product is a β-amino thioester. Also, the 2-hydroxyphenylamino group in the product can be converted to a primary amino group by removing the aryl group with a method using CAN (ceric ammonium nitrate).

Hydrazone

Instead of the above-mentioned imine, a benzoylhydrazone represented by the following formula (V):

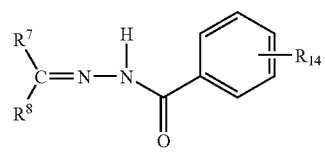

(V)

wherein, $R^7$ and $R^8$, not being the same, are selected from the group consisting of a hydrogen atom, a hydrocarbon group, and a hydrocarbon group having a functional group and $R^{14}$ represents a hydrogen atom or a substituent having an electron-withdrawing property; may be used as the reaction substrate. In this situation, it is preferable that either $R^7$ or $R^8$ is a hydrogen atom. Also, examples of substituents having an electron-withdrawing property which are used as $R^{14}$ include halogens, perfluoroalkyl groups having at most 4 hydrocarbons, and nitro groups.

A β-hydrazinocarbonyl compound having, for example, the following structure:

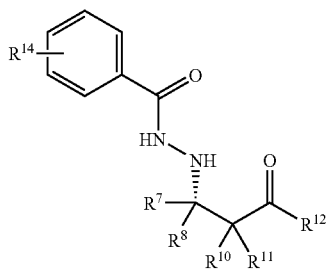

can be obtained by using the asymmetric niobium catalyst of the present invention when the above-mentioned benzoylhydrazone and the above-mentioned silicon enolate are used. This product can be converted to a primary amino group by breaking the N—N bond using samarium oxide or Raney nickel.

Epoxide Ring-Opening Reaction Using a Nucleophilic Agent

The catalyst of the present invention can be applied to an epoxide ring opening reaction using a nucleophilic agent in which the epoxide is an electrophilic agent. There are no particular limitations to the structure of the epoxide.

Examples include a compound represented by the following formula (VII):

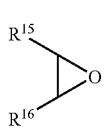

(VII)

wherein $R^{15}$ and $R^{16}$ are selected from the group consisting of a hydrogen atom, a aliphatic hydrocarbon group, an aromatic hydrocarbon group, and a hydrocarbon group having a substituent, with the proviso that either $R^{15}$ or $R^{16}$ is not a hydrogen atom and R15 and R16 may form at least a 5-membered ring structure.

Examples of the nucleophilic agent include azides, primary amines, secondary amines, thiols, cyano compounds, and halides. Among these, nitrogen-containing compounds are preferable. In particular, primary and secondary amines are preferable.

Other Nucleophilic Addition Reactions

The asymmetric reaction catalyst of the present invention can be used in a nucleophilic addition reaction by a nucleophilic agent other than a silicon enolate for the above-mentioned imine or the above-mentioned acylhydrazone. For example, asymmetric allylation reactions by an allylation agent such as allyltrichlorosilane and asymmetric cyanation reactions by trialkyl tin cyanide or the like can be carried out.

Reaction Method

There are no particular limitations to the method for adding the reaction substrate to the above-mentioned catalyst.

Generally, the imine or the like, which has been dissolved in a solvent, is added dropwise to a solution including the above-mentioned catalyst and a solution including the nucleophilic agent may then be added dropwise. The reaction temperature can by arbitrarily selected according to the type of reaction substrate. Normally, the temperature is −78° C. to room temperature and preferably −40° C. to 0° C. The reaction time is generally 1 to 72 hours. The concentration of the reaction substrate in the reaction system including the above-mentioned catalyst and solvent is preferably 0.05 to 1.0 mol/l and more preferably 0.1 to 0.5 mol/l.

For example, after an imine compound or the like dissolved in a halogen hydrocarbon such as methylene chloride is added dropwise to the solution containing the above-mentioned catalyst, the nucleophilic agent may then be added dropwise.

When the catalyst of the present invention is used in an asymmetric reaction in which the above-mentioned nucleophilic agent is nucleophilically added to the above-mentioned reaction substrate, very high enantioselectivity is shown and various amine compounds can be obtained in high optical purity. For example, a β-aminoketone (right-hand side formula (VI)) in the above-mentioned formula) with at least 70% chemical yield and at least 90% optical yield can be obtained in most situations by the Mannich reaction. The compounds of formula (III) and (IV) in the left-hand side of the above-mentioned formula are an imine compound and a silicon enolate, respectively, already shown by chemical formulas. The contents represented by reference symbols such as $R^3$ are as already mentioned.

Below, the present invention will be specifically explained using examples and comparative examples. However, these do not limit the present invention. The NMR spectra ($^1$H-NMR, $^{13}$C-NMR) were measured using JEOL-LA300, JEOL-LA400, or JEOL-LA500 (NMR (nuclear magnetic resonance) spectrometers manufactured by JEOL Ltd.). Optical rotation was measured using JASCO P-1010 (polarimeter manufactured by JASCO Corporation). The IR spectra were measured using FT/IR-610 (Fourier transform IR spectrometer manufactured by JASCO Corporation).

1. Experiment 1

Example 1

Preparation of Triol Having Binapthol Structure

A triol was prepared in accordance with the reaction formula shown in FIG. 1.

Firstly, sodium hydride (275 mmol) was suspended in tetrahydrofuran (THF) (120 ml) and to this, 2-isopropylphenol (111 mmol, reference symbol A1 in FIG. 1) dissolved in THF (30 ml) was added dropwise at 0° C. After 30 minutes, chloromethyl methyl ether (221 mmol) was added to this solution and after heating to room temperature, the reaction was stopped by adding methanol and then water. The aqueous phase was extracted with ether. The organic phases were combined and washed with water and a saturated sodium chloride solution in that order and then dried using anhydrous sodium sulfate. After removing the drying agent by filtering, the solvent was distilled off under reduced pressure. The residue was purified by silica gel chromatography to obtain 1-isopropyl-2-methoxy methoxybenzene (17.5 g, 87% yield, reference symbol A2 in FIG. 1).

At −78° C., a hexane solution of n-butyl lithium (100 mmol/64 ml) was added dropwise to a THF (200 ml) solution including 15.0 g (83 mmol) of the above-mentioned compound A2 and 15 ml (100 mmol) of tetramethylethylenediamine (TMEDA). After 30 min, the solution was heated to 0° C., stirred for 1 hour, and again cooled to −78° C. Dimethylformamide (DMF) (15.9 ml) was then added dropwise. After the reaction solution was slowly heated to room temperature, the reaction solution was poured into a saturated aqueous solution of ammonium chloride. The aqueous phase was extracted with ether. The organic phases were combined and washed with water and a saturated sodium chloride solution in that order and then dried using anhydrous sodium sulfate. After removing the drying agent by filtering, the solvent was distilled off under reduced pressure. The residue was purified by silica gel chromatography to obtain 3-isopropyl-2-methoxy methoxybenzaldehyde (12.9 g, 74% yield, reference symbol A3 in FIG. 1).

$^1$H-NMR δ(ppm): 1.25 (d, 6H, J=7.1 Hz), 3.40 (sept, 1H, J=7.1 Hz), 3.60 (s, 3H), 5.06 (s, 1H), 7.25 (dd, 1H, J=7.6, 7.6 Hz), 7.55 (dd, 1H, J=1.7, 7.6 Hz), 7.70 (dd, 2H, J=1.7, 7.6 Hz), 10.3 (s, 1H)

Next, after a hexane solution of n-butyl lithium (45.4 mmol/28.9 ml) was added dropwise at room temperature to an ether (450 ml) solution containing (R)-2,2'-bis(methoxymethoxy)-[1,1']binaphthalene (37.9 mmol, reference symbol A4 in FIG. 1) and TMEDA (45.1 mmol), the solution was stirred for 1.5 hours. After the mixed solution was cooled to −78° C., an ether (50 ml) solution of the above-mentioned product A3 (22.9 mmol) was added dropwise. After the reaction solution was slowly heated to room temperature, the reaction solution was poured into a saturated aqueous solution of ammonium chloride. The aqueous phase was extracted with ether. The organic phases were combined and washed with water and a saturated sodium chloride solution in that order and then dried using anhydrous sodium sulfate. After removing the drying agent by filtering, the solvent was distilled off under reduced pressure. The residue was purified by silica gel chromatography to give approximately a 1:1 diastereomeric ratio of (R)-(2,2'-dimethoxy-methoxy[1,1']binaphthyl-3-yl)-(3-isopropyl-2-methoxymethoxyphenyl)methanol (12.2 g, 92% yield, reference symbol A5 in FIG. 1).

Under ice-cooling, hydrogen chloride-saturated methanol (35 ml) was added to a dichloromethane (35 ml) solution of the above-mentioned product A5 (21 mmol) and stirred for 2 hours. The mixed solution was neutralized by the addition of a saturated aqueous solution of sodium hydrogen carbonate and the organic phase was separated. The aqueous phase was extracted with methylene chloride. The organic phases were combined and washed with water and a saturated sodium chloride solution in that order and dried using anhydrous sodium sulfate. After removing the drying agent by filtering, the solvent was distilled off under reduced pressure. At 0° C., triethylsilane (67.2 mmol) was added to a methylene chloride (100 ml) solution of the obtained crude alcohol (A6 in FIG. 1). Next, a boron trifluoride-ether complex (65.1 mmol) was added dropwise. After the reaction solution was stirred overnight, the reaction solution was neutralized by adding a saturated aqueous solution of sodium hydrogen carbonate. The organic phase was separated. The remaining aqueous phase was extracted with methylene chloride. The organic phases were combined and washed with water and a saturated sodium chloride solution in that order and then dried with anhydrous sodium sulfate. After removing the drying agent by filtering, the solvent was distilled off under reduced pressure. The residue was purified by silica gel chromatography to give the final product [(R)-3-(2-hydroxy-3-isopropylbenzyl)-[1,1']binaphthalene 2,2'-diol] (6.2 g, 68% yield, 2 steps, reference symbol A7 in FIG. 1).

$^1$H-NMR δ (ppm): 1.20 (d, 3H, J=6.8 Hz), 1.21 (d, 3H, J=6.8 Hz), 3.25 (sept, 1H, J=6.8 Hz), 4.17 (d, 1H, J=14.9 Hz), 4.23 (d, 1H, J=14.9 Hz), 4.99 (s, 1H), 5.63 (s, 1H), 6.51 (s, 1H), 6.90 (ddd, 1H, J=1.5, 7.5, 7.5 Hz), 7.08-7.11 m, 3H), 7.22-7.39 (m, 6H), 7.82 (d, 1H, J=7.9 Hz), 7.88 (d, 1H, J=8.1 Hz), 7.93 (s, 1H), 7.97 (d, 1H, J=9.0 Hz)

$^{13}$C-NMR (CDCl$_3$) δ (ppm): 22.5, 22.8, 27.1, 31.5, 108.9, 110.6, 111.5, 117.8, 120.6, 124.1, 124.2, 124.5, 124.9, 125.9, 127.1, 127.6, 128.0, 128.1, 128.5, 128.8, 129.5, 129.9, 131.2, 131.7, 132.2, 133.2, 135.8, 149.8, 151.1, 152.8.

$[α]_D^{30}$: +63.6 (c 1.03, THF)

Mp: 205-206° C.

IR (KBr): 3505, 3425, 1592, 1463, 820, 751 cm$^{-1}$

Asymmetric Nucleophilic Addition Reaction of a Ketene Silyl Acetal to an Aldimine Using an Asymmetric Reaction Catalyst 1. Preparation of Reaction Substrate and Nucleophilic Agent The imine (aldimine) prepared by recrystallizing the product prepared from the corresponding aldehyde and phenol derivative in dichloromethane and DMF and also in the presence of molecular sieves was used as the reaction substrate. The silyl enolate (silyl enol ether) was synthesized according to the method disclosed by S. Kobayashi et al. in "Silyl Enol Ethers", in *Science of Synthesis: Houben-weyl Methods of Molecular Transformations*, George Thieme Verlag, Stuttgart, 2002, Vol. 4, p. 317. The other chemicals used in the reaction were all purchased commercial products and were purified according to necessity. The reaction was completely performed under an argon atmosphere.

2. Preparation of Catalyst

The above-mentioned product A6 (72 μmol) was dissolved in toluene (0.3 ml). To this solution was added a toluene (0.6 ml) solution of N-methylimidazole (NMI) (60 μmol) at room temperature and stirred. After this mixed solution was stirred for 10 min, a toluene (0.6 ml) solution of Nb(OMe)$_5$ (60 μmol) was added. After heating to 60° C. and stirring for 3 hours, the mixed solution was then returned to room temperature. This mixed solution was transferred to a flask having molecular sieves 3A (100 mg) and after being washed with methylene chloride (0.5 ml), was stirred for 30 minutes.

3. Asymmetric Reaction

The above-mentioned solution was cooled to −20° C. and a methylene chloride (0.7 ml) solution of the imine represented by the following formula IV:

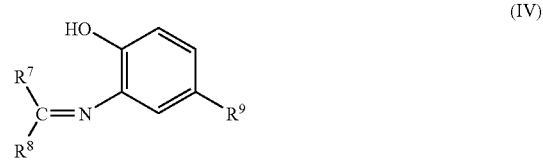

(IV)

(0.6 mmol, R$^7$=Ph, R$^8$=H, R$^9$=H) and then a methylene chloride (0.3 ml) solution of the silyl enol ether represented by the following formula VI:

(VI)

(0.72 mmol, R$^{10}$=R$^{11}$=R$^{13}$=Me, R$^{12}$=OMe) were added. After stirring for 48 hours, the reaction was stopped by pouring the reaction solution into a saturated aqueous solution of sodium hydrogen carbonate. The aqueous phase was extracted with methylene chloride. The above-mentioned aqueous phase and organic phase were combined, washed with water and a saturated sodium chloride solution in that order, and then dried with anhydrous sodium sulfate. After removing the drying agent by filtering, the solvent was distilled off under reduced pressure. The obtained crude product was purified using preparation thin layer chromatography (benzene/ethyl acetate=9/1) and an aminoketone derivative (product) represented by the following formula:

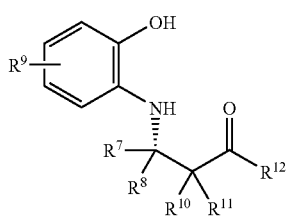

was obtained (yield 86%, $R^7$ to $R^{10}$=same as in the above-mentioned formulas IV and V, a hydroxyl group and not a methoxy group is connected to the benzene). The asymmetric yield (99% ee) of the product was determined by HPLC (high-performance liquid chromatography) using a chiral column.

Various Properties of Products

Name: (S}-methyl 2,2'-dimethyl-3-(2-hydroxyphenyl)amino-3-phenylpropionate

IR (KBr): 3401, 1709, 1611, 1514, 1453, 1391 cm$^{-1}$.

$^1$H-NMR (CDCl$_3$): δ (ppm): 1.21 (s, 3H), 1.24 (s, 3H), 3.68 (s, 3H), 4.57 (s, 1H), 6.36-6.76 (m, 4H), 7.21-7.28 (m, 5H).

$^{13}$C-NMR (CDCl$_3$): δ 19.9, 24.2, 47.3, 52.1, 64.3, 113.2, 114.1, 117.6, 120.8, 127.3, 127.9, 128.3, 135.6, 138.9, 144.0, 178.0.

HPLC (Daicel Chiralpak AD, hexane/$^i$PrOH=9/1, flow rate=1.0 ml/min, $t_R$=9.3 min (3R), $t_R$=16.0 min (3S). Anal. Calcd for $C_{18}H_{21}NO_3$: C, 72.22; H, 7.07; N, 4.68. found: C, 72.28; H, 7.20; N, 4.62.

HRMS: Calcd for $C_{18}H_{21}NO_3$ (M$^+$) 299.1522, found 299.1497.

Absolute configuration of S-configuration of product: determined by X-ray crystal structure analysis of the corresponding camphor acid ester.

Examples 2 to 10

In each of the compounds in the above-mentioned formulas IV and VI, apart from $R^7$ to $R^{13}$ being changed to the products shown in Table 1, the reactions were performed the same as in Example 1. The chemical yields and asymmetric yields of the compounds are shown in Table 1.

TABLE 1

| | Formula (III) | | | Formula (IV) Ketene Silyl Acetal | | | | Reaction Product Yields (%) | |
|---|---|---|---|---|---|---|---|---|---|
| | Imine | | | | | | | Chemical | Asymmetric |
| | $R^7$ | $R^8$ | $R^9$ | $R^{10}$ | $R^{11}$ | $R^{12}$ | $R^{13}$ | Yield | Yield |
| Example 1 | H | Ph | H | Me | Me | OMe | Me | 86 | 99% ee |
| Example 2 | H | (4-Cl)C$_6$H$_4$ | H | Me | Me | OMe | Me | 82 | 98% ee |
| Example 3 | H | (4-OMe)C$_6$H$_4$ | H | Me | Me | Ome | Me | 79 | 96% ee |
| Example 4 | H | 1-Naphthyl | H | Me | Me | Ome | Me | 40 | 95% ee |
| Example 5 | H | 2-Naphthyl | H | Me | Me | Ome | Me | 77 | 98% ee |
| Example 6 | H | 3-Thienyl | H | Me | Me | Ome | Me | 85 | 93% ee |
| Example 7 | H | Ph | CF$_3$ | Me | Me | Ome | Me | 75 | 91% ee |
| Example 8 | H | Ph | H | H | H | SEt | Me | 69 | 84% ee |
| Example 9 | H | (4-Cl)C$_6$H$_4$ | H | H | H | SEt | Me | 44 | 88% ee |
| Example 10 | H | 2-Furyl | H | H | H | SEt | Me | 70 | 87% ee |

As shown in Table 1, when an imine was used in the reaction substrate of each of the Examples, a high asymmetric yield of approximately 90% of the corresponding β-aminoketone derivative was obtained by a nucleophilic addition reaction using silyl enolate as the nucleophilic agent. Thus, it was understood that a nucleophilic reaction having high enantioselectivity to an imine is possible. The properties of the reaction products (aminoketone derivatives) obtained in Examples 2 to 10 are shown below.

Example 2

(S)-methyl 3-(4-chlorophenyl)-2,2'-dimethyl-(2-hydroxyphenyl)aminopropionate

IR (KBr) 3359, 1709, 1610, 1513, 1490, 1450, 738 cm$^{-1}$.

$^1$H-NMR (CDCl$_3$): δ (ppm) 1.19 (s, 3H), 1.24 (s, 3H) 3.67 (s, 3H), 4.55 (s, 1H), 6.31-6.90 (m, 4H), 7.22 (s, 2H), 7.35 (s, 2H).

$^{13}$C-NMR (CDCl3): δ (ppm) 20.2, 24.7, 47.3, 52.4, 64.0, 113.3, 114.3, 117.9, 121.1, 128.2, 128.3, 129.7, 133.2, 135.4, 137.7, 144.0, 177.5.

HPLC: measuring conditions same as Example 1, $t_R$=8.3 min (3R), $t_R$=16. 7 min (3S). Anal. Calcd for $C_{18}H_{20}NO_3Cl$: C, 64.77; H, 6.04; N, 4.20. found: C, 64.47; H, 6.18; N, 4.01.

HRMS: Calcd for $C_{18}H_{20}NO_3Cl$ (M+) 333.1133, found 333.1109.

Example 3

Methyl 2,2'-dimethyl-3-(2'-hydroxyphenylamino)-3-(4'-methoxyphenyl) propionate

IR (neat): 3420, 2979, 1715, 1612, 1510, 1252 cm$^{-1}$.

$^1$H-NMR (CDCl$_3$): δ (ppm) 1.20 (s, 3H), 1.22 (s, 3H), 3.68 (s, 3H), 3.76 (s, 3H), 4.50 (s, 1H), 6.39 (d, 1H, J=7.9 Hz), 6.35 (dd, 1H, J=7.6, 7.6 Hz), 6.62 (dd, 1H, J=7.6, 7.6 Hz}, 6.68 (d, 1H, J=7.9 Hz), 6.81 (d, 1H, J=8.5 Hz), 7.19 (d, 1H, J=8.5 Hz).

$^{13}$C-NMR (CDCl$_3$): δ (ppm) 20.1, 24.4, 47.5, 52.2, 55.2, 64.2, 113.4, 114.3, 115.3, 117.2, 118.1, 119.7, 121.1, 129.4, 131.0, 135.6, 144.4, 158.8, 177.8.

HPLC: measuring conditions same as Example 1, tR=11.1 min (3R), tR=28.0 min (3S).

HRMS: Calcd for $C_{19}H_{23}NO_4$ (M$^+$) 329.1627, found 329.1638.

Example 4

(S)-methyl 2,2'-dimethyl-3-(2-hydroxyphenyl)amino 3-(1'-naphthyl)-propionate $^1$H-NMR (CDCl$_3$): δ (ppm) 1.18 (s, 3H), 1.25 (s, 3H) 3.66 (s, 3H), 5.62 (s, 3H), 6.28-6.62 (m, 4H), 7.22-8.00 (m, 7H).

$^{13}$C-NMR (CDCl$_3$): δ (ppm) 19.9, 25.1, 48.4, 52.4, 57.8, 113.4, 114.2, 117.9, 121.2, 122.1, 123.2, 125.2, 125.3, 125.4, 126.1, 128.1, 129.1, 133.6, 135.3, 144.1, 177.9.

HPLC: apart from using chiralcel AD in the column, measuring conditions same as Example 1, $t_R$=14.6 min (3s), $t_R$=10.6 min (3R).

Anal. Calcd for C$_{22}$H$_{23}$NO$_3$: C, 75.62; H, 6.63; N, 4.01. found: C, 75.48; H, 6.49; N, 3.94.

HRMS: Calcd for C$_{18}$H$_{20}$NO$_3$Cl (M+) 349.1678, found 349.1668.

Example 5

Methyl 2,2'-dimethyl-3-(2'-hydroxyphenyl)amino-3-(2'-naphthyl) propionate

IR (KBr) 3418, 1710, 1610, 1510, 1270, 736 cm$^{-1}$.
$^1$H-NMR (CDCl$_3$): δ (ppm) 1.26 (s, 3H), 1.29 (s, 3H), 3.70 (s, 3H), 4.71 (s, 1H), 6.40-6.70 (m, 4H) 7.41-7.46 (m, 3H), 7.75-7.81 (m, 4H).
$^{13}$C-NMR (CDCl$_3$): δ (ppm) 20.2, 24.5, 47.6, 52.3, 64.8, 114.0, 114.3, 118.0, 121.1, 125.8, 126.2, 127.5, 127.6, 127.6, 127.9, 132.9, 133.0, 135.5, 136.7, 144.3, 177.7.

HPLC: apart from the flow rate being 0.8 ml/min, measuring conditions same as Example 1, $t_R$=12.2 min (3R), $t_R$=26.0 min (3S).

HRMS: Calcd for C$_{22}$H$_{23}$NO$_3$ (M+) 349.1678, found 349.1671.

Example 6

(R)-methyl 3-(2-hydroxyphenyl)amino-2,2'-dimethyl-3-(3'-thienyl)propionate

IR (neat) 3413, 2978, 1708, 1608, 1513, 1446, 1267, 1192, 1140, 741 cm$^{-1}$.
$^1$H-NMR (CDCl$_3$): δ (ppm) 1.25 (s, 3H), 1.28 (s, 3H), 3.69 (s, 3H), 4.66 (s, 1H), 6.46-6.71 (m, 4H), 6.98 (d, 1H J=5.6 Hz), 7.06 (s, 1H), 7.21 (s, 1H).
$^{13}$C-NMR (CDCl$_3$): δ (ppm) 20.4, 24.1, 47.2, 52.2, 61.2, 114.5, 115.1, 118.9, 121.1, 122.9, 125.2, 127.3, 135.3, 140.7, 145.0, 177.7.

HPLC: measuring conditions same as Example 1, $t_R$=9.2 min (3S), $t_R$=14.3 min (3R).

Example 7

(S)-methyl 3-(2-hydroxy-5-trifluoromethylphenyl)amino-2,2'-dimethyl-3-phenylpropionate IR (neat) 1707, 1612, 1531, 1442, 1336, 1277, 1115 cm$^{-1}$.
$^1$H-NMR (CDCl$_3$): δ (ppm) 1.22 (s, 3H), 1.26 (s, 3H), 3.70 (s, 3H), 4.54 (s, 1H), 6.58 (s, 1H), 6.75 (d, 2H, J=7.6 Hz), 7.23-7.32 (m, 5H).
$^{13}$C-NMR (CDCl$_3$): δ (ppm) 20.2, 24.7, 47.3, 52.4, 64.5, 109.9, 113.6, 115.0, 123.2, 123.5, 127.8, 128.2, 135.7, 138.3, 137.0, 146.6, 177.9.

HPLC: measuring conditions same as Example 1, $t_R$=5.4 min (3R), $t_R$=7.3 min (3S).

Anal. Calcd for C$_{19}$H$_{20}$F$_3$NO$_3$: C, 62.12; H, 5.49; F, 15.11; N, 3.81; O, 13.07. found: C, H, N.

Example 8

(S)—S-ethyl 3-(2-hydroxyphenyl)amino-3-phenylpropanthioic acid

IR (KBr) 3396, 1647, 1608, 1520, 1449, 1362 cm$^{-1}$.
$^1$H-NMR (CDCl$_3$): δ (ppm) 1.67 (t, 3H, J=7.3 Hz), 2.83 (q, 2H, J=7.3 Hz), 2.97 (dd, 1H, J=5.4, 14.9 Hz), 3.07 (dd, 1H, J=8.1, 14.9 Hz), 4.81 (dd, 1H, J=5.4, 8.1 Hz), 6.44-6.71 (m, 4H), 7.20-7.33 (m, 5H).
$^{13}$C-NMR (CDCl$_3$): δ (ppm) 14.4, 23.6, 51.4, 56.1, 114.4, 114.6, 118.8, 121.1, 126.3, 127.4, 128.6, 134.9, 141.7, 144.7, 198.4.

HPLC: apart from using chiralpak AS in the column and hexane/$^i$PrOH=19/1, measuring conditions same as Example 1, $t_R$=26.6 min (3S), $t_R$ 38.2 min (3R). Anal. Calcd for C$_{17}$H$_{19}$NO$_2$S: C, 67.74; H, 6.35; N, 4.65. found: C, 68.00; H, 6.54; N, 4.54.

HRMS: Calcd for C$_{17}$H$_{19}$NO$_2$S (M$^+$) 301.1138, found 301.1102.

Example 9

(S)—S-ethyl 3-(4'chlorophenyl)-3-(2-hydroxyphenyl)amino-phenylpropanthioic acid

IR (neat) 3412, 1665, 1516, 144 7, 742 cm$^{-1}$.
$^1$H-NMR (CDCl$_3$): δ (ppm) 1.21 (t, 2H J=7.4 Hz), 2.83 (q, 2H J=7.4 Hz), 2.96 (dd, 1H, J=5.1, 14.9 Hz), 3.05 (dd, 1H, J=8.3, 14.9 Hz), 4.78 (dd, 1H, J=5.1, 8.3 Hz), 6.39-6.78 (m, 4H), 7.22-7.28 (m, 5H).
$^{13}$C-NMR (CDCl$_3$): δ (ppm) 14.5, 23.7, 51.2, 55.6, 114.5, 115.0, 119.3, 121.2, 127.8, 128.9, 133.2, 134.6, 140.3, 144.7, 197.8.

HPLC: measuring conditions same as Example 1, $t_R$=19.5 min (3S), $t_R$=24.3 min (3R). Anal. Calcd for C$_{17}$H$_{18}$NO$_2$ClS: C, 60.80; H, 5.40; N, 4.17. found: C, 60.85; H, 5.60; N, 3.99.

HRMS: Calcd for C$_{17}$H$_{18}$NO$_2$ClS (M+) 335.0747, found 335.9758.

Example 10

(S)—S-ethyl 3-(2'-furyl)-3-(2-hydroxyphenyl)amino-phenylpropanthioic acid

IR (neat) 3414, 1674, 1608, 1513, 1448, 1349, 740 cm$^{-1}$.
$^1$H-NMR (CDCl$_3$): δ (ppm) 1.32 (t, 3H, J=7.3 Hz), 2.90 (q, 2H, J=7.3 Hz), 3.06 (dd, 1H, J=5.4, 15.6 Hz), 3.19 (dd, 1H J=8.3, 15.6 Hz), 4.81 (dd, 1H J=5.4, 8.3 Hz), 6.11 (d, 1H J=3.2 Hz), 6.26 (dd, 1H J=2.0, 3.2 Hz), 6.60-6.81 (m, 4H), 7.35 (d, 1H J=2.0 Hz).
$^{13}$C-NMR (CDCl$_3$): δ (ppm) 14.5, 23.6, 48.0, 50.8, 106.8, 110.2, 115.0, 118.0, 120.7, 121.5, 133.8, 142.0, 147.1, 153.8, 198.2.

HPLC: measuring conditions same as Example 4, $t_R$=15.4 min (3S), $t_R$=8.9 min (3R). Anal. Calcd for C$_{18}$H$_{17}$NO$_3$S: C, 61.83; H, 5.88; N, 4.81. found: C, 61.86; H, 5.72; N, 4.80.

HRMS: Calcd for C$_{15}$H$_{17}$NO$_3$S (M$^+$) 291.0932, found 291.0931.

2. Experiment 2

Aminolysis Reaction Between Niobium Alkoxide and an Epoxide Having an Optically-Active Tetradentate Binaphthol Structure Under an argon atmosphere, a toluene (0.60 ml) solution of niobium methoxide (0.040 mmol) was added at room temperature to a toluene (0.40 ml) solution of a tetradentate binaphthol structure (optically-active tetraol) (0.044 mmol), stirred for 3 hours at 60° C., and then returned to room temperature to become a toluene solution of a chiral niobium complex.

(Synthesis of Tetradentate Binaphthol)

Figure 2:
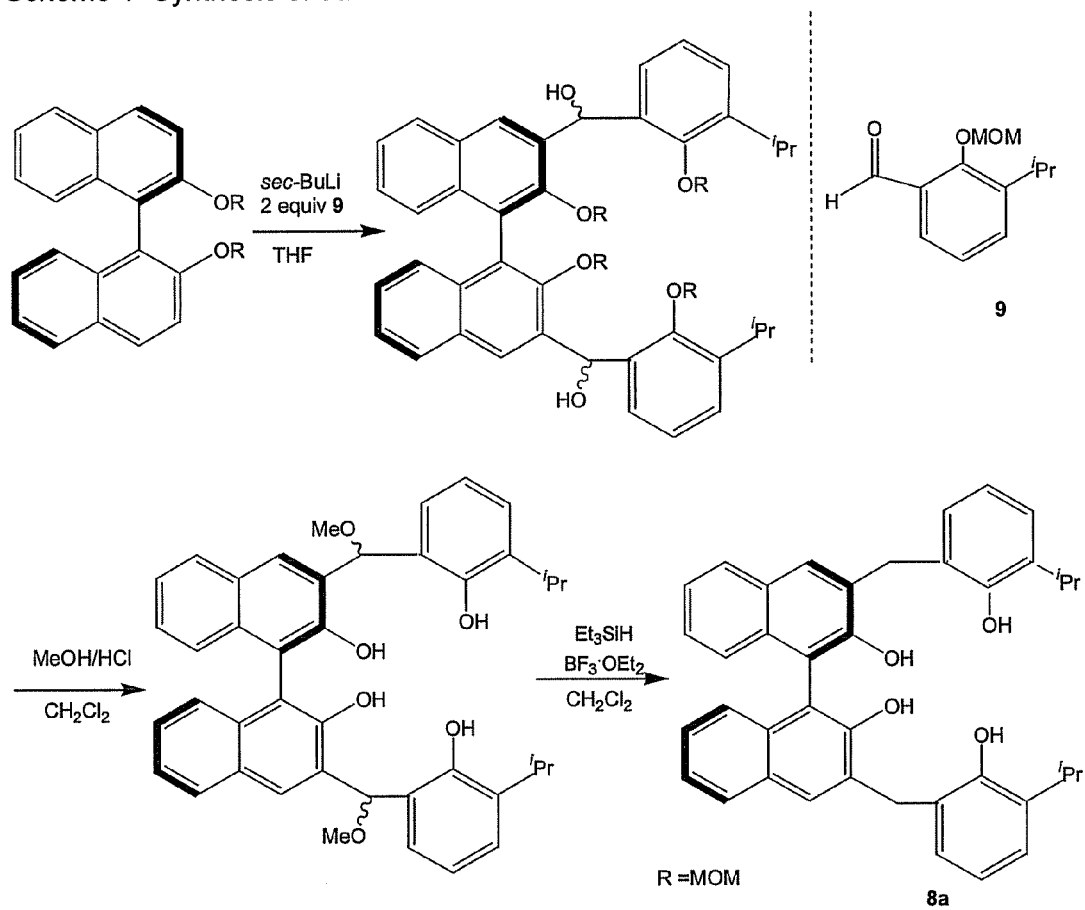
FIG. 2 shows a reaction scheme in order to prepare a tetraol having a binaphthol structure.

The synthesis scheme of the tetradentate binaphthol is shown in FIG. 2.

(R)-3,3'-bis(2-hydroxy-3-isopropylbenzyl)[1,1']binaphthalene-2,2'-diol (8a): After a THF solution (90 ml) of (R)-2,2'-bis(methoxy-methyloxy)-1,1'-binaphthalene (5.33 g, 14.23 mmol) was cooled to −78° C., a sec-butyl lithium hexane solution (0.99 M, 28.4 ml, 28.1 mmol) was added dropwise thereto and then stirred for 30 minutes. After increasing the temperature to 0° C., the solution was further stirred for 1.5 hours and then cooled to −78° C. A THF solution (30 ml) of 3-isopropyl-2-methoxymethoxybenzaldehyde (11.85 g, 56.9 mmol) was added dropwise thereto, the temperature was increased to room temperature, and stirred overnight. The reaction was stopped by using an aqueous saturated ammonium chloride solution and extracted with diethyl ether. The combined organic phases, after being washed with water and a saturated sodium chloride solution, were dried using anhydrous sodium sulfate. The solvent was distilled off under reduced pressure and the residue was purified by silica gel chromatography to obtain approximately a 1:1 diastereomer mixture of (R)-(2,2'-dimethoxy-methoxy[1,1']binaphthyl-3-yl)-(3-isopropyl-2-methoxymethoxyphenyl)methanol (11.28 g) was obtained. This alcohol (11.28 g) was made into a methylene chloride solution (120 ml), stirred at 0° C., and a saturated hydrogen chloride methanol solution (45 ml) was then added. After stirring for 30 minutes, the reaction solution was neutralized using saturated sodium bicarbonate water and extracted with methylene chloride. The combined organic phases were washed with water and the solvent was distilled off under reduced pressure. The residue was not purified and was dissolved in methylene chloride (70 ml). After being cooled to 0° C., a methylene chloride solution (35 ml) of triethylsilane (8.62 g, 74.1 mmol) and a methylene chloride solution (35 ml) of a boron trifluoride and diethyl ether complex (10.72 g, 75.5 mmol) were added dropwise in that order and then stirred overnight at 0° C. The reaction was stopped using saturated sodium bicarbonate water and extracted with methylene chloride. The combined organic phases were washed with water and a saturated sodium chloride solution and then dried using anhydrous sodium sulfate. The solvent was distilled off under reduced pressure and the residue was purified by silica gel chromatography to obtain (R)-3,3'-bis(2-hydroxy-3-isopropylbenzyl)-[1,1']binaphthalene-2,2'-diol (5.76 g, 9.89 mmol, 69% yield in 3 steps) was obtained.

(R)-3,3'-bis(2-Hydroxy-3-isopropylbenzyl)-[1,1')binaphthalene-2,2'-diol (8a): $[\alpha]_D^{20}$+38.9 (c 1.01, CHCl$_3$) • Mp 115-117° C. IR (KBr) 3445, 2959, 1626, 1451, 1208, 1088, 753 cm$^{-1}$. $^1$H-NMR (CDCl$_3$): δ 1.22 (d, 12H, J=8.0 Hz), 3.25 (sept, 2H, J=6.8 Hz), 4.19 (d, 4H, J=15.1 Hz), 5.67 (s, 2H), 6.46 (s, 2H), 6.91 (dd, 2H, J=7.5, 7.5 Hz), 7.05 (d, 2H, J=8.1 Hz), 7.23 (m, 6H), 7.35 (dd, 2H, J=8.0 Hz), 7.82 (d, 2H, J=8.01 Hz), 7.93 (s, 2H). $^{13}$C-NMR (CDCl$_3$): δ 22.6, 22.7, 27.1, 31.5, 111.4, 120.7, 124.0, 124.6, 124.9, 125.8, 127.2, 128.1, 128.1, 128.9, 129.9, 131.3, 132.0, 135.8, 149.9, 151.1. HPLC Daicel Chiralpak AD-H, hexane/$^i$PrOH=19/1, flow rate 1.0 ml/min: $t_R$=13.1 min (S), $t_R$=15.8 min (R).

MS: Calcd for C$_{40}$H$_{38}$O$_4$ (M$^+$+Na$^+$) 605, found 605.

Anal. Calcd for C$_{15}$H$_{17}$NO$_3$S: C, 61.83; H, 5.88; N, 4.81. found: C, 61.86; H, 5.72; N, 4.80.

(Reaction)

The optically active tetraol 8a shown in FIG. 2 was used.

In a different reaction vessel, dried molecular sieves 4A (100 mg) were added and after making the atmosphere an argon atmosphere, the chiral niobium complex toluene solution prepared above was transferred to this reaction vessel using a cannula and washed with toluene (0.50 ml). This was stirred at room temperature for 30 minutes and then cooled to 200° C. A methylene chloride solution (0.50 ml) of an epoxide (cyclohexene oxide) (0.40 mmol) and a methylene chloride solution (0.50 ml) of an amine (aniline) (0.48 mmol) were added in that order and then stirred for 18 hours. The reaction was stopped by adding a saturated aqueous sodium hydrogen carbonate solution (10 ml) and the aqueous phase was extracted with methylene chloride (10 ml×3). The organic phases were combined and dried using anhydrous sodium sulfate. The solvent was distilled off under reduced pressure and the residue was purified using silica gel thin layer chromatography (Hexane:AcOEt 4:1) to obtain the corresponding α-amino alcohol ((1R,2R)-2-(phenylamino)cyclohexanol. The optical purity of this product was determined by HPLC using an enantiomer separation column (Daicel Chiralpak AD).

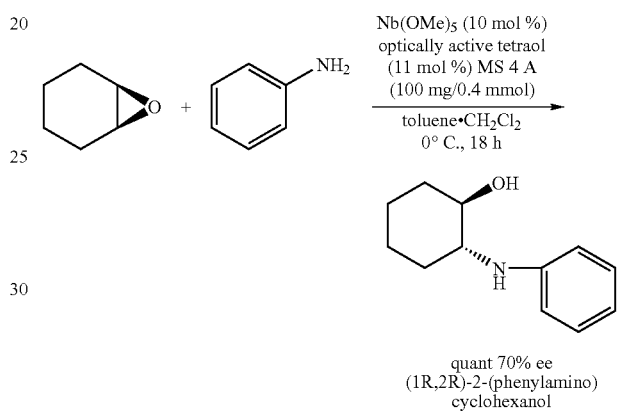

quant 70% ee
(1R,2R)-2-(phenylamino)cyclohexanol

The chemical yield of the α-amino alcohol, which is the product, was quantitative and the asymmetric yield (hereinafter referred to as ee) was 70%.

3. Experiment 3

Epoxide Aminolysis Reaction According to Type of Binaphthol Structure

Under an argon atmosphere, a methylene chloride solution (0.60 ml) of the below niobium alkoxide (0.040 mmol) was added to a toluene solution (0.40 ml) of the below binaphthol structures 1a to 1c at room temperature (a toluene solution only was used for the binaphthol structure 1c) and then stirred for 3 hours at 60° C. The solution was then returned to room temperature and became a toluene solution of a chiral niobium complex.

-continued

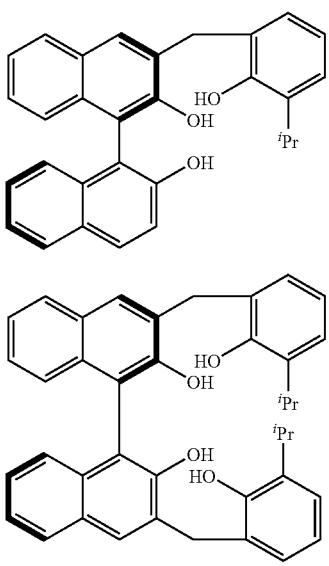

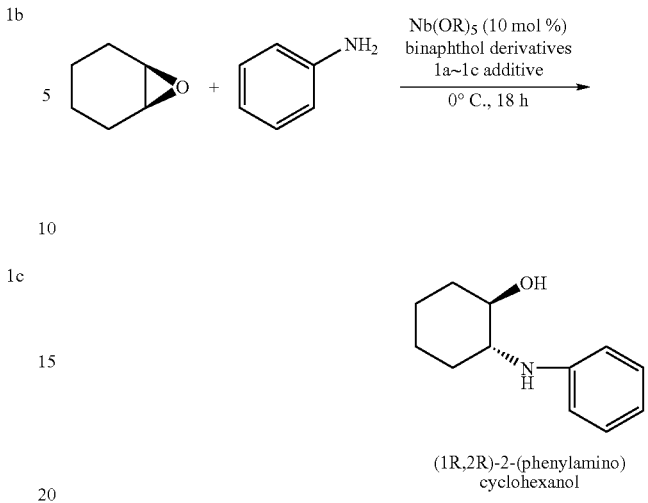

(1R,2R)-2-(phenylamino)
cyclohexanol

The results obtained are shown in Table 2. In the table, R represents the alkyl group of niobium alkoxide.

TABLE 2

| Binaphthol Derivative 1 | R | Additive | Solvent | Yield (%) | ee (%) |
|---|---|---|---|---|---|
| 1a (22 mol %) | —CH(CH$_3$)$_2$ | none | CH$_2$Cl$_2$ | 69 | 48 |
| 1b (11 mol %) | —CH(CH$_3$)$_2$ | 2,2'-biphenol (11 mol %) 2,6-lutidine (12 mol %) | CH$_2$Cl$_2$ | 55 | 48 |
| 1c (11 mol %) | -Me | MS 4A | CH$_2$Cl$_2$-toluene | quant | 70 |

The above-mentioned compounds 1c and 8a are the same.

To a different reaction vessel was added a given additive and after making the atmosphere a argon atmosphere, the chiral niobium complex methylene chloride (toluene) solution prepared above was transferred to this reaction vessel using a cannula and washed with methylene chloride (toluene for the binaphthol structure 1c) (0.50 ml). This was stirred for 30 minutes at room temperature and cooled to 0° C. A methylene chloride solution (0.50 ml) of an epoxide (cyclohexene oxide) (0.40 mmol) and a methylene chloride solution (0.50 ml) of an amine (aniline) (0.48 mmol) were added in that order and then stirred for 18 hours. An additive was not used with the binaphthol structure 1a and dried molecular sieves 4A (100 mg) were used as the additive for the binaphthol structure 1c.

The reaction was stopped by adding a saturated aqueous sodium hydrogen carbonate solution (10 ml) and the aqueous phase was extracted with methylene chloride (10 ml×3). The organic phases were combined and dried using anhydrous sodium sulfate. The solvent was distilled off under reduced pressure and the residue was purified using silica gel thin layer chromatography (Hexane:AcOEt 4:1) to obtain the corresponding α-amino alcohol ((1R,2R)-2-(phenylamino)cyclohexanol. The optical purity of this product was determined by HPLC using an enantiomer separation column (Daicel Chiralpak AD).

The reaction conditions were suitable conditions for each of the optically active binaphthol derivatives As is clear from Table 2, when a tetraol is used as the binaphthol structure, the chemical yield and stereoselectivity of the epoxide asymmetric ring opening are the highest. It is thus proved that the use of a tetraol is effective in epoxide asymmetric ring opening.

What is claimed is:

1. An asymmetric reaction catalyst obtained by mixing a pentavalent niobium compound and tetraol having an optically active binapthol structure of R or S configuration, wherein the asymmetric reaction catalyst can catalyze an asymmetric reaction selected from the group consisting of an asymmetric Mannich reaction, an epoxide asymmetric ring opening reaction, an asymmetric allylation reaction, an asymmetric cyanation reaction and an asymmetric alkylation reaction.

2. An asymmetric reaction catalyst according to claim 1, wherein the niobium compound is represented by the following formula:

NbX$_5$ (wherein, X is an alkoxide or a halogen atom).

3. An asymmetric reaction catalyst according to claim 1, wherein the tetraol is represented by the following formula (III):

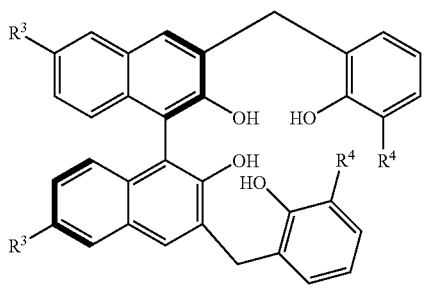

(III)

wherein $R^3$ represents a hydrogen atom, a halogen atom, a perfluoroalkyl group having at most 4 carbons, or an alkyl group or alkoxy group having at most 4 carbons and $R^4$ represents a hydrogen atom or a hydrocarbon group having 1 to 10 carbons.

4. An asymmetric reaction catalyst according to claim 2, wherein the tetraol is represented by the following formula (III):

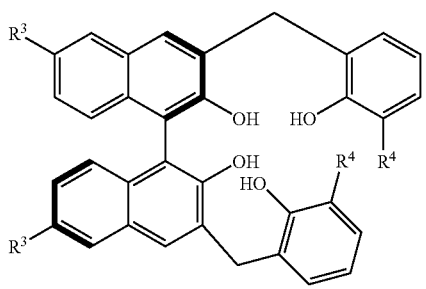

(III)

wherein $R^3$ represents a hydrogen atom, a halogen atom, a perfluoroalkyl group having at most 4 carbons, or an alkyl group or alkoxy group having at most 4 carbons and $R^4$ represents a hydrogen atom or a hydrocarbon group having 1 to 10 carbons.

5. A method for preparing an optically active compound, wherein a reaction substrate represented by $R^5R^6C=N-Z$ (wherein $R^5$ and $R^6$, not being the same, are selected from the group consisting of a hydrogen atom, a hydrocarbon group, an alkoxycarbonyl group, and a hydrocarbon group having a functional group and Z represents an aryl group or an acylamino group) and a nucleophilic agent are reacted by nucleophilic addition using an asymmetric reaction catalyst according to claim 1.

6. A method for preparing an optically active compound according to claim 5, wherein the above-mentioned reaction substrate is an imine represented by the following formula (IV):

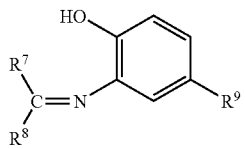

(IV)

wherein $R^7$ and $R^8$, not being the same, are selected from the group consisting of a hydrogen atom, a hydrocarbon group, and a hydrocarbon group having a functional group and $R^9$ represents a hydrogen atom or a trifluoromethyl group.

7. A method for preparing an optically active compound according to claim 5, wherein the above-mentioned nucleophilic agent is a silicon enolate represented by the following formula (VI):

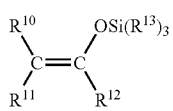

(VI)

wherein $R^{10}$ and $R^{11}$ are each independently one selected from the group consisting of a hydrogen atom, an aliphatic hydrocarbon group, an aromatic hydrocarbon group, an alkyloxy group, an aryloxy group, and an silyloxy group; $R^{12}$ is one selected from the group consisting of a hydrogen atom, an aliphatic hydrocarbon group, an alkyloxy group, an aryloxy group, an arylthio group, and a alkylthio group; and each $R^{13}$, being the same or different, represents a hydrocarbon group.

8. A method for preparing an optically active compound according to claim 5, wherein an imidazole derivative is added to the reaction system.

9. A method for preparing a optically active compound wherein a reaction substrate and a nucleophilic agent are reacted by nucleophilic addition using an asymmetric reaction catalyst according to claim 1.

10. A method for preparing an optically active compound according to claim 9, wherein the reaction substrate is an epoxide, the nucleophilic agent is a nitrogen compound, and the optically active compound is a nitrogen-containing compound.

* * * * *